United States Patent [19]

Van Eck et al.

[11] 4,342,184
[45] Aug. 3, 1982

[54] METHOD OF MANUFACTURE OF HYPODERMIC SYRINGE

[76] Inventors: William F. Van Eck, 300 Main St., East Haven, Conn. 06512; Maurits J. H. Van Eck, 70 Jerome Cresent, PHO, Stoney Creek, Ontario, Canada

[21] Appl. No.: 137,528

[22] Filed: Apr. 4, 1980

Related U.S. Application Data

[60] Continuation-in-part of Ser. No. 869,288, Jan. 13, 1978, abandoned, which is a division of Ser. No. 723,192, Sep. 15, 1976, Pat. No. 4,130,117, which is a division of Ser. No. 501,448, Aug. 28, 1974, Pat. No. 3,989,045, which is a continuation of Ser. No. 293,489, Sep. 29, 1972, abandoned.

[51] Int. Cl.³ .................. B65B 43/00; B65B 51/14
[52] U.S. Cl. .................... 53/452; 53/561; 53/574; 53/268; 264/524; 264/537; 425/524

[58] Field of Search .............. 53/452, 561, 425, 453, 53/454, 477, 574, 561, 268; 264/524, 525, 537; 425/524

[56] References Cited

U.S. PATENT DOCUMENTS

| | | | |
|---|---|---|---|
| 3,162,706 | 12/1964 | Cheney | 264/525 |
| 3,251,915 | 5/1966 | Pechthold | 53/452 X |
| 3,301,928 | 1/1967 | Plymale | 264/537 |
| 3,330,894 | 7/1967 | Valyi | 264/537 |
| 3,792,144 | 2/1974 | Burkett et al. | 264/525 |
| 3,851,029 | 11/1974 | Cornett et al. | 264/525 |
| 3,855,380 | 12/1974 | Gordon et al. | 264/537 X |
| 3,936,264 | 2/1976 | Cornett et al. | 425/388 X |

Primary Examiner—Horace M. Culver
Attorney, Agent, or Firm—Robert H. Montgomery

[57] ABSTRACT

A method of manufacture of pre-filled ampuls and hypodermic needles where an ampul is formed by injection-moulding and blow-moulding. The ampul is filled with medicaments at the blow-moulding stage and a hypodermic needle is then affixed to the ampul.

21 Claims, 10 Drawing Figures

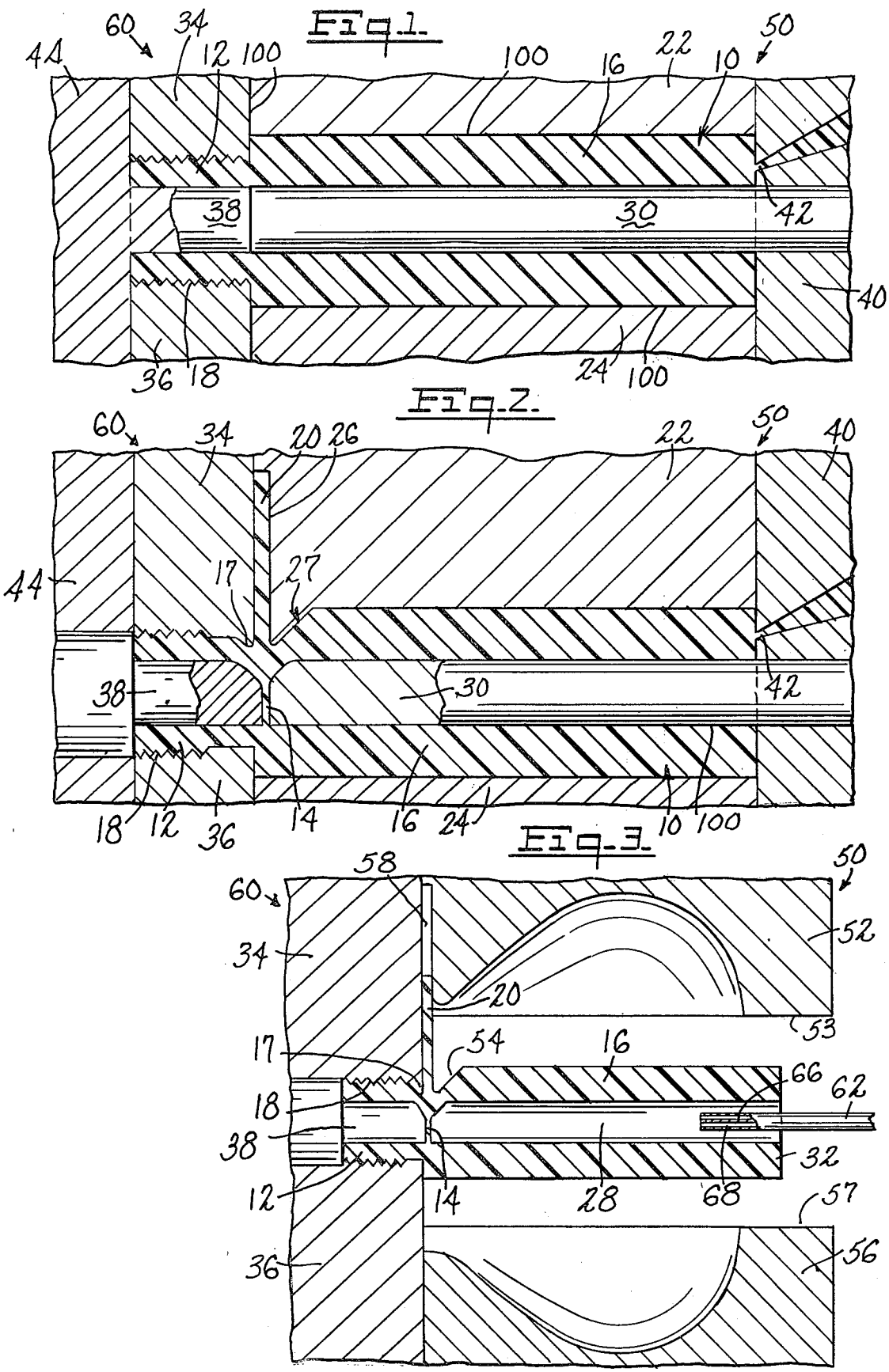

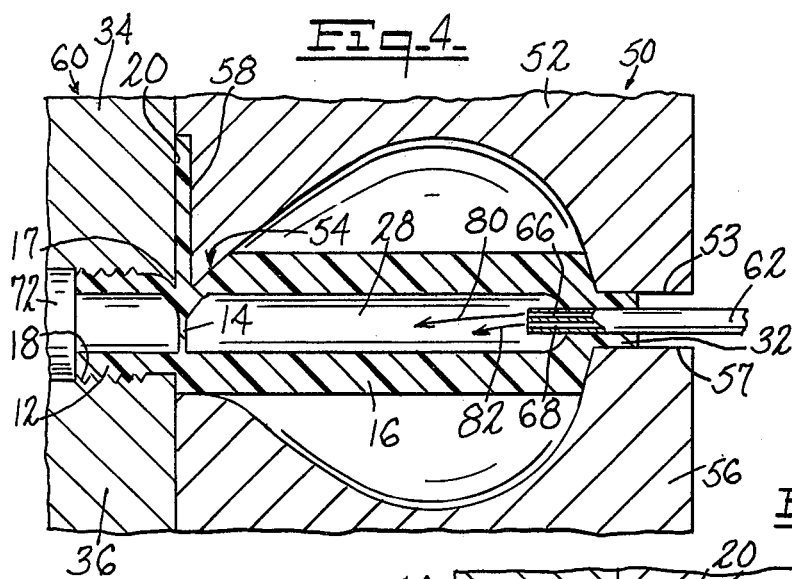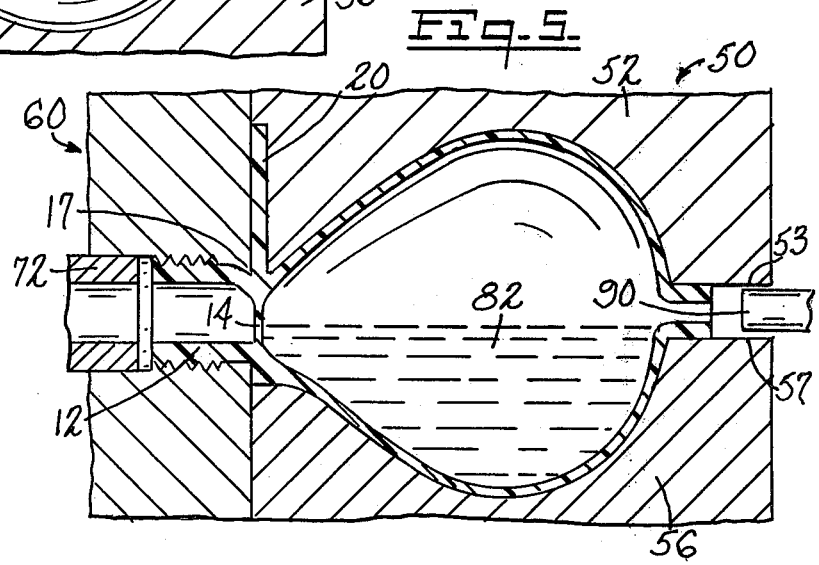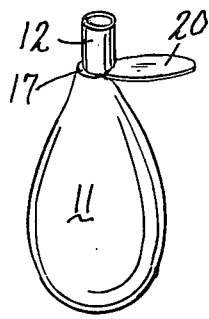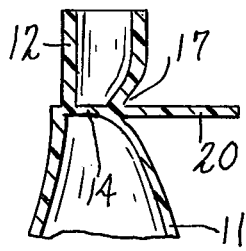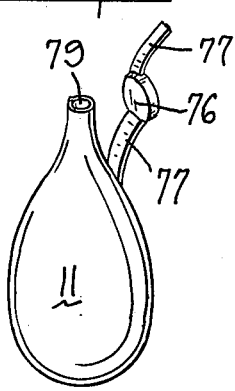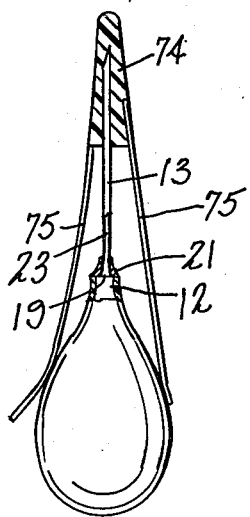

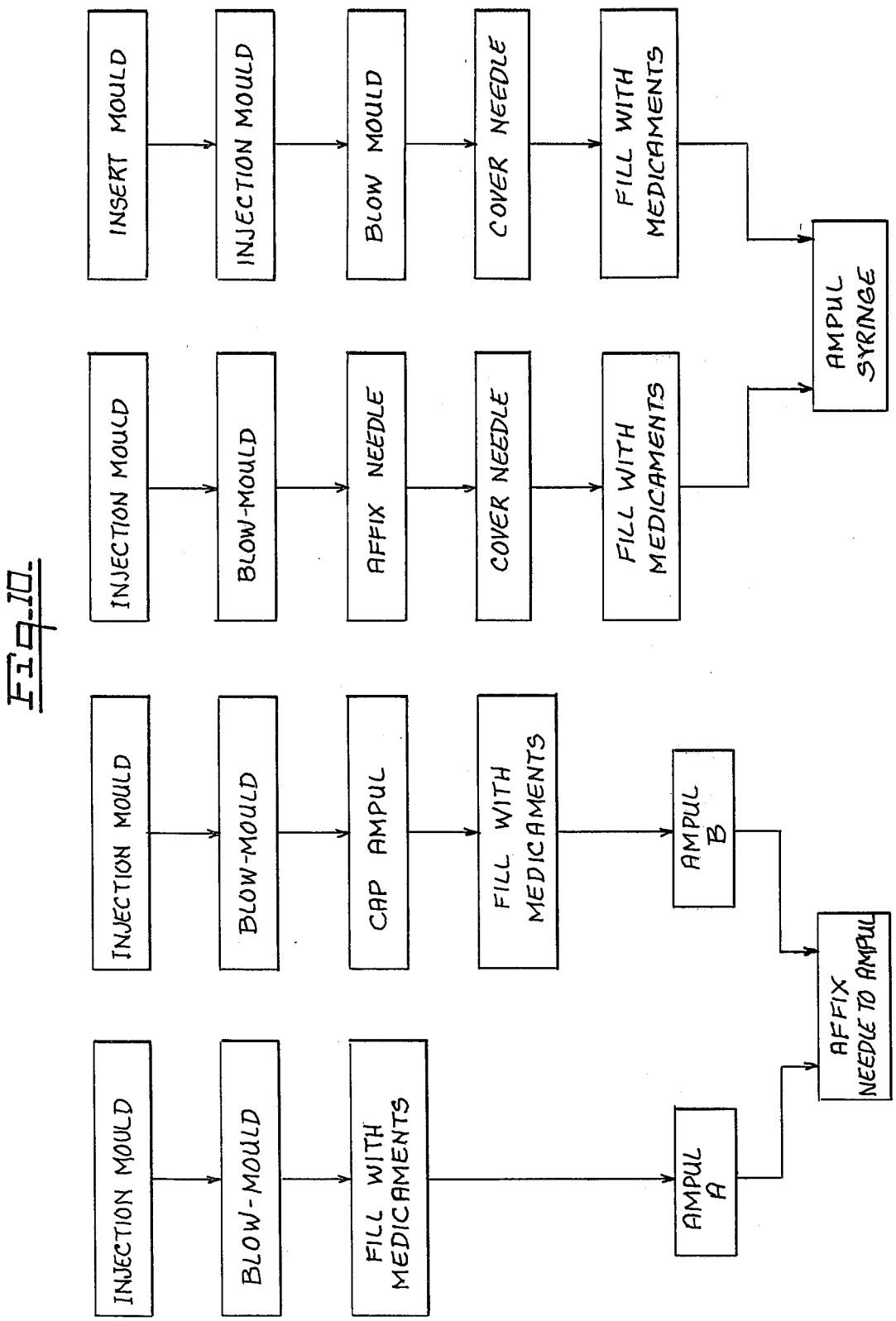

METHOD OF MANUFACTURE OF HYPODERMIC SYRINGE

This application is a continuation-in-part of Application Ser. No. 869,288, filed Jan. 13, 1978, and now abandoned, which was a division of Application Ser. No. 723,192, filed Sept. 15, 1976, now U.S. Pat. No. 4,130,117 which was in turn a division of Application Ser. No. 501,448, filed Aug. 28, 1974, now U.S. Pat. No. 3,989,045, which was a continuation of Application Ser. No. 293,489, filed Sept. 29, 1972, now abandoned.

BACKGROUND OF THE INVENTION

This invention relates to a method for manufacturing a pre-filled hypodermic syringe. More particularly, the invention relates to a method of manufacturing a pre-filled ampul adapted for use with a hypodermic needle and a method for manufacturing a hypodermic syringe composed in part of a pre-filled ampul.

Pre-filled flexibly structured hypodermic syringes consisting of a hypodermic needle and an ampul have been disclosed in issued U.S. Pat. No. 3,989,045 to Van Eck. These disclosed ampuls are formed from resin or other thermoplastic materials, so as to provide a resiliency or memory whereby the ampul resumes its original shape after compression.

The method which is the subject of the present invention provides an improved process of manufacturing the ampuls and syringes disclosed in U.S. Pat. No. 3,989,045 and other similar hypodermic syringes and ampuls.

Previous methods of manufacturing and filling hypodermic syringes have generally segregated the manufacturing, sterilizing, and filling stages. Such processes of manufacture are unsatisfactory with respect to rates of production as manufacturing methods for pre-filled ampuls and syringes, especially of the type disclosed in U.S. Pat. No. 3,989,045.

This invention provides a new and improved method which differs from previous methods of manufacturing pre-filled hypodermic syringes in that the ampul is formed, filled with medicaments and bonded to the hypodermic needle and/or ready for affixation of the hypodermic needle at a later time, all in a single continuous efficient process. All of the steps and procedures may be accomplished within a single tooling apparatus. Moreover, the sterility of the contents of the ampul and the sterility of the hypodermic syringe itself is maintained throughout the process.

SUMMARY OF THE INVENTION

The new and improved method in one form comprises initially the injection-moulding of plastic to form a neck and a parison. The neck is in final form at the injection stage. A blow-fill pin is inserted into the parison, and the parison is then blow-moulded into the final shape of the ampul. Medicaments are injected into the ampul through the blow-fill pin. The pin is then removed from the ampul. The opening left upon the removal of the pin is closed by means such as sonic welding. The temperatures of the injection-moulding and the blow-moulding, as well as other procedures, help to insure the sterility of the medicaments. Alternate embodiments of the manufacturing process involve the sealing of a cap over the opening in the neck area of the ampul. Further embodiments of the process involve the affixing of a hypodermic needle to the ampul. The latter step may be accomplished by a variety of techniques as hereinafter described.

An object of this invention is to provide a new and improved method of manufacturing an ampul adapted for use in a pre-filled hypodermic syringe.

Another object of this invention is to provide for a new and improved method of manufacturing and filling flexibly structured ampuls and hypodermic syringes within a single tooling apparatus in a continuous process.

A further object of this invention is to provide for a new and improved method of manufacturing and filling flexibly structured ampuls and hypodermic syringes while maintaining the sterility of the contents throughout the process.

A still further object of this invention is to provide a new and improved method that permits the manufacture of pre-filled ampuls and hypodermic syringes at increased rates of production.

BRIEF DESCRIPTION OF THE DRAWINGS

FIG. 1 is a horizontal cross-sectional view showing a preform at the injection-moulding station;

FIG. 2 is a horizontal cross-sectional view showing another embodiment of a preform at the injection-moulding station;

FIG. 3 is a horizontal cross-sectional view of the preform of FIG. 2 prior to the closing of moulds at the blow-moulding station;

FIG. 4 is a horizontal cross-sectional view of the preform of FIG. 2 after the moulds of the blow-moulding station have been closed around a blow-fill pin;

FIG. 5 is a vertical cross-sectional view of the neck and ampul at the blow-moulding station after the ampul has been formed and the blow-fill pin retracted;

FIG. 6 is a vertical sectional view of a type-C ampul/syringe;

FIG. 7 is an isometric view of a type-A ampul;

FIG. 8 is a vertical cross-sectional view of a type-A ampul;

FIG. 9 is an isometric view of a type-B ampul; and

FIG. 10 is a block diagram outlining the major steps of the manufacturing method.

DETAILED DESCRIPTION

The new and improved method is preferably accomplished by means of a multi-station tooling apparatus which is capable of performing coordinated multiple functions at a given station and, in addition, the tooling apparatus is capable of transfering a workpiece from station to station in a continuous coordinated manner.

For purposes of understanding the tooling apparatus, it should be noted that at each station a movable assembly interacts with a stationary assembly.

The movable assembly can function to transfer a workpiece from one station to another. The workpiece transfer may be accomplished by rotation of the workpiece from one station to another. The movable assembly, in addition, may comprise sub-assembly components which interact with the stationary assembly to perform various steps in the manufacturing process.

The stationary assembly is so designated because it remains at a given position within the tooling apparatus with respect to other stations. The stationary assembly itself may, however, be movable with respect to the workpiece and may provide for a number of coordinated mechanized functions.

A parting line 100 designates the surfaces where the stationary assembly components and the movable assembly components contact each other and separate from each other. It should be noted that the workpiece normally separates from the stationary assembly upon transfer to another station. Such a separation may be in the form of the stationary assembly being retracted away from a workpiece or the workpiece being removed from the stationary assembly by the movable assembly, and/or a combination of these parting processes.

A station may comprise a multiplicity of mould components which move relative to each other in the manufacturing process. The mould components which close to form the mould cavities at various stations in the tooling apparatus and which open up to allow for the removal of the workpiece or to allow for the accomplishment of other procedures in the manufacturing process are engineered so that there may be multiple axes of closing and opening the moulds. The parting lines at a station may therefore be significantly more complex than conventional parting lines determined by opening and closing symmetrical mould halves.

The new and improved method which is the subject of this invention can best be appreciated by first referring to FIG. 10, which shows by means of block diagrams the various forms of the method. The preferred form of the method which is used to produce and manufacture an ampul of the type which has been designated Ampul A. An example of ampul type A is shown in FIGS. 7 and 8. While all the forms of the new and improved method set forth are specifically directed to syringes and ampuls which are the subject of U.S. Pat. No. 3,989,045, the new and improved method has applications and is suitable for the manufacture of ampuls and syringes other than those disclosed in U.S. Pat. No. 3,989,045.

A type A ampul is an ampul which has a barrier membrane formed in the neck of the ampul, which membrane is adapted to be easily ruptured at the time of use to permit the communication of the medicaments with the hypodermic syringe needle. An additional property of a type A ampul is an ampul wall structure which is a complete surface continuum without discernible discontinuities even at the intersection of the barrier membrane with the neck.

The first step in the manufacturing of the type A ampul is the injection-moulding of a preform 10 as shown in FIG. 2. The injection-moulding station comprises a stationary assembly 50 and a movable assembly 60. A parting line 100 designates the interface between the stationary assembly and the movable assembly.

The preform 10 consists of a solid structure referred to hereinafter as neck 12 and a parison 16. A barrier membrane 14 is formed at the intersection of the neck and the parison. An indentation 17 is formed in the preform at the barrier membrane and an appendage 20 is formed exteriorly adjacent to the membrane 14. Threaded grooves 18 annularly envelop the neck.

The previously-described shape of the preform is defined by the mould configurations which are formed at the injection-moulding station. The interior channel of the neck 12 is formed by means of a neck pin 38, which is of a generally cylindrical shape. The exterior of the neck is formed by neck moulds 34 and 36. The front portion of the neck is formed by a front mould 44. It should be noted that the foregoing moulds are all elements of the moveable assembly.

A parison cavity 28 is determined by means of a core pin 30. The core pin 30 is in general alignment with the neck pin 38. The relative axial separation between pins 38 and 30 determines the thickness of the membrane 14. Parison moulds 22 and 24 act to form the exterior of the parison at the preform stage. Parison mould 22 is further provided with an appendage slot 26 and indentation mould 27. The ends of the parison are formed by a rear mould 40.

Neck moulds 34 and 36 and parison moulds 22 and 24 cooperate to form cylindrical cavities in the movable assembly and the stationary assembly, respectively. While it is possible that neck moulds 34 and 36 and parison moulds 22 and 24 may be in the form of unitary mould structures or substantially identical mould halves which push together to form the cylindrical cavities, such moulds may be composed of precision tooled, matched, non-symmetrical, multi-part components which interact and move along a multiplicity of axes.

Thermoplastic material such as polyethylene or similar material which is characterized by low-level hexane extractables and low porosity is injected into the preform cavity at gate 42. It should be noted that the gate 42 may be in such vertical orientation with respect to the preform cavity that the thermoplastic material moves through the mould form to assume the shape of the preform partly by gravitational means. However, additional pressure is normally required to insure proper uniformity and quality. It the gate is at a horizontal orientation with respect to the preform mould cavity, as illustrated in FIG. 2, pressure is required at the injection gate, to force the thermoplastic material to fill the entire preform mould cavity and to insure uniformity.

It should be noted that at the injection-moulding station the parison does not set up into its final form, but remains in a viscous-like state. This state is generally insured by means of circulating hot oil inside the core pin. The neck 12, the appendage 20, and the barrier membrane 14 are essentially formed and assume final structural characteristics at the injection-moulding station.

The preform or workpiece is next transferred to the blow-moulding station, which is illustrated in FIG. 3. A blow-fill pin 62 is inserted into the parison cavity 28 from a position opposite the neck end of the preform. Blow moulds 52 and 56 are closed around the still viscous parison. Mould ends 53 and 57 crunch the parison ends 32 together to form a continuum of the surface of the parison. The only breach of the continuum is the blow-fill pin 62. Blow mould 52 is further machined to allow for appendage slot 58 and mould indentation 54, which fit against the appendage 20 and the indentation 17, respectively. The bulbous cavity formed by the closing together of blow mould forms 52 and 56 defines the final outer shape of the ampul 11.

The blow-fill pin 62 comprises a gas bore 66 and a fill bore 68. The bores may be arranged in a concentric configuration or the bores may be axially spaced. A blow gas 80 which may be in the form of sterilized air is forced out of the gas bore 66 and blows the viscous parison to a thin bulbous structure which is defined by the blow moulds 52 and 56. During the blow-mould stage, the viscous parison is gradually shaped and transformed into the final solid ampul embodiment.

Medicaments 82 are then injected into the parison through the fill bore 68. The blow gas 80 is evacuated through the gas bore 66. The quantity of medicament 82 is accurately metered. If pin 62 is at the horizontal position illustrated in FIGS. 3 and 4, the medicament will not escape from the ampul provided the quantity of medicament is less than half the volume of the ampul as further indicated in FIG. 5. It should be noted that other orientations of the blow mould station are possible in which case the blow-fill pin 62 could be inserted into the parison from a position above the parison and there would be little chance of escape of the medicament 82, provided the volume of medicament was less than the volume of the final ampul. Typically, medicaments occupy approximately half of the interior volume of the completed ampuls.

Upon retraction of pin 62 from the newly formed ampul, normally a breach is left in the wall of the ampul. The wall structure of the ampul in final form is such that there are no structural discontinuities and, in particular, no discrete seals, or boundaries in the wall structure. To accomplish such structural quality and to close the breach, a sonic welding probe 90 is positioned in the vicinity of the breach left by the removal of the blow-fill pin as shown in FIG. 5. The sonic welding probe 90 energizes the plastic molecules in the vicinity of the breach, so as to establish a wall continuum. Preferably, the ampul wall in the vicinity of the breach is relatively thick prior to the sonic welding so that the energized molecules will flow to form a continuum of substantially uniform thickness. Typical specifications call for the sonic probe to be brought within one-tenth of an inch from the ampul and the energizing time interval to be on the order of three-tenths of a second.

The integration of the blow mould and fill stages by means of the previously described blow-fill pin procedures may be varied so that the gas bore 66 and fill bore 68 are separate structures and are inserted and retracted at different positions with respect to the parison/ampul and at different times.

The blow-fill pin operation and the sonic welding may be accomplished at the blow-mould station or the ampul may be rotated or transferred from the blow-mould station to another station for purposes of accomplishing the injection of medicaments and/or the establishing of the wall continuum by means of sonic welding.

At this point, the ampul is completely formed, filled with medicaments and the medicaments are completely isolated from outside contamination. A stripper sleeve 72 ejects the completed ampul from the tooling apparatus. A hypodermic needle may be affixed to the ampul at a later time. Grooves 18 facilitate the affixing of the hypodermic needle.

Sterilization of the ampul in all embodiments of the method is provided by the operating temperatures during the injection and blow-mould stages and the unique integration of the steps of forming and filling the ampul. Upon the completion of the final ampul form and the injection of medicaments, the interior of the ampul is isolated from external contamination. The sterilization of the blow-fill pin and the medicaments prior to injection into the ampul is accomplished by standard procedures.

A general outline for the manufacturing process of a type B ampul is outlined in the second column of the block diagram of FIG. 10. A type B ampul essentially refers to an ampul as disclosed in U.S. Pat. No. 3,989,045 in which the opening or aperture 79 in the neck is closed by means of a cap 76 as illustrated in FIG. 9.

The injection-moulding station comprises essentially the same elements as the corresponding injection-moulding station employed for the type A ampul with the exception of the appendage slot 26 and indentation mould 27. In addition, core pin 30 and neck pin 38 contact each other as shown in FIG. 1 or alternately a single pin may be employed instead of pins 30 and 38.

Thermoplastic material is injected at gate 42 into the cavity formed by the moulds at the injection-moulding station. It should be noted that gate 42 may be positioned through end mould 44 in the case of a type B ampul process rather than the gate position of FIG. 1. The preform 10 at this station also consists of a neck 12 in final form and a parison 16 which remains in a viscous state.

The preform is rotated or transferred to the blow-mould station (not shown for type B). The blow-mould station employed for the type B ampul comprises the same mould structure as the previously-described type A blow-mould structures, with the exception of the mould indentation 54 and the appendage slot 58 which are, of course, not necessary in view of the fact that the type B ampul has neither an appendage 20 nor an indentation 17. The blow-mould ends 53 and 57 crunch the ends of the parison 32 around a pin 67 (not shown) containing a gas bore 66. A blow gas is injected through the gas bore 66, which gas blows the viscous parison into a thin bulbous ampul structure whose exterior surface is defined by means of the blow-mould 52 and 56 in a manner similar to the process for a type A ampul.

Pin 67 is retracted from the newly formed ampul leaving a small breach in the surface continuum of the ampul. Mould components 52 and 56 open up and retract from the ampul and the workpiece now consisting of the formed neck and ampul is transferred to a closing station.

The breach is closed by means of sonic welding which may be accomplished immediately after retraction of pin 67 or the breach may be closed simultaneously with the closing of the breach left upon retraction of pin 69 described below.

At the closing station, a cap 76 which has previously been moulded is placed over aperture 79, so as to completely seal the ampul except for the breach left by the pin 67. The sealing of the cap may be insured by heat sealing cap sleeves 77 to the exterior of the ampul. Such sealing may be accomplished by sonic welding.

A fill pin 69 (not shown) having a fill bore 68 is inserted in the wall of the ampul. The point of insertion is preferably the thickest part of the ampul wall and may be at or near the insertion point of pin 67. Medicaments are carefully metered and injected through the fill bore 68 into the ampul. Fill pin 69 is retracted from the ampul, and the surface continuum of the ampul is established by means of sonic welding. The medicaments are now completely isolated from outside contamination.

The hypodermic needle may be affixed to the filled ampul at a later time. In many cases it is preferable to affix the needle to the ampul just prior to use of the syringe.

Further alternate embodiments of the manufacturing process are outlined in columns three and four of FIG. 10. These latter embodiments are used in conjunction with the manufacturing of a hypodermic syringe where the needle is affixed to the ampul during the manufacturing process. This latter type of hypodermic syringe designated as ampul/syringe C is illustrated in FIG. 6.

One method involving the affixation of the hypodermic needle proceeds as in the previously-described process with respect to the injection-moulding and blow-moulding stages. After the blow-moulding stage, a hypodermic needle 13 is attached at the neck 12 of the ampul. The hypodermic needle is seated into the neck structure 12. A sonic welding probe is positioned in the vicinity of the needle base 21/neck 12 interface. The probe is energized so as to sonically bond the needle base 21 to the neck 12.

The hypodermic needle is then sealed by means of placing a cover assembly 74 over the hypodermic needle 13. The cover assembly is preferably a moulded structure, and the assembly 74 is secured in place by means of either heat sealing or sonic welding cover sleeves 75 to the body of the ampul 11.

The ampul is then filled with medicaments and the ampul wall continuum is established by means of the steps previously outlined for ampul B.

Another manufacturing process which involves the affixation of the hypodermic syringe involves the initial step of insert moulding of the hypodermic syringe needle. A hypodermic needle is positioned at the injection-moulding station, so that the hypodermic needle base 21 forms an interior mould for the neck. Thermoplastic material injected at the injection-moulding station flows around the base of the hypodermic syringe, and bonds the hypodermic needle 13 to the neck 12. This latter process is a form of insert moulding.

Care must be taken so that the internal passage 23 of the hypodermic needle is not blocked. The latter may be accomplished by bringing the core pin 30 into sealing contact at the opening 19 in the hypodermic syringe base.

The injection-moulding stages and blow-moulding stages are carried out as previously outlined in the prior two embodiments. After the blow-moulding stage, the needle is covered as outlined in the previous embodiment. The ampul is filled with medicine and the ampul wall continuum is established as also previously outlined.

It will thus be seen that the objects set forth above, among those made apparent from the preceding description, are efficiently attained and since certain changes may be made in the above manufacturing process without departing from the spirit and scope of the invention, it is intended that all matter contained in the above description or shown in the accompanying drawings shall be interpreted as illustrative of the invention and not in a limiting sense.

What we claim is:

1. A method for manufacturing and filling an ampul adapted for use with a hypodermic needle to form a hypodermic syringe, said method comprising:
    (a) injection-moulding a preform comprising a neck at one end and a parison having an open end at other end of said preform;
    (b) closing said open end around a blow-fill pin;
    (c) blow-moulding the parison into the form of an ampul;
    (d) introducing medicament into said ampul through said pin;
    (e) withdrawing said pin from said ampul; and
    (f) establishing an integral wall continuum of said ampul after withdrawal of said pin.

2. A method according to claim 1 and further comprising the injection-moulding of a barrier membrane, said membrane positioned in the interior of the neck.

3. The method according to claim 2 in which an indentation is moulded in the neck at the location of the barrier membrane, said indentation being in the form of an inwardly directed fold in said neck.

4. A method according to claim 2 in which an appendage is moulded to the outside of said neck, said appendage being aligned with said barrier membrane.

5. A method according to claim 1 wherein step (f) is accomplished by means of sonic welding.

6. A method for manufacturing and filling an ampul adapted for use with a hypodermic needle to form a hypodermic syringe, said method comprising:
    (a) injection-moulding a preform comprising a neck at one end having an aperture and a parison having an open end at the other end of said preform;
    (b) closing said open end around a blow-fill pin;
    (c) blow-moulding said parison into the form of an ampul;
    (d) closing said aperture;
    (e) introducing medicament into said ampul through said pin;
    (f) withdrawing said pin from said ampul; and
    (g) establishing an integral wall continuum of said ampul after withdrawal of said pin.

7. The method according to claim 6 wherein the step of closing said aperture comprises covering said aperture with a cap.

8. A method according to claim 7 wherein the cap is secured to the ampul by means of sonic welding.

9. A method according to claim 6 wherein step (g) is accomplished by means of sonic welding.

10. A method for manufacturing and filling an ampul adapted for use with a hypodermic needle to form a hypodermic syringe, said method comprising:
    (a) injection-moulding a preform comprising a neck at one end and a parison having an aperture at the other end;
    (b) blow-moulding said parison into the form of an ampul;
    (c) closing said aperture;
    (d) inserting a fill pin into said ampul through the wall thereof;
    (e) introducing medicament into said ampul through said pin;
    (f) withdrawing said pin from said ampul; and
    (g) establishing an integral wall continuum of the ampul after withdrawal of said pin.

11. A method according to claim 10 wherein the step of closing said aperture comprises the covering of said aperture with a cap.

12. A method according to claim 11 wherein the cap is secured to the ampul by means of sonic welding.

13. A method for manufacturing and filling a hypodermic syringe, said method comprising:
    (a) injection-moulding a preform comprising a neck portion at one end and a parison at the other end;
    (b) blow-moulding said parison into the form of an ampul;
    (c) affixing a hypodermic needle to said neck;
    (d) covering said hypodermic needle;
    introducing a medicament through the wall of said ampul; and
    (f) establishing an integral wall continuum of said ampul at the point of introduction.

14. A method according to claim 13 wherein a hypodermic needle is affixed to said neck by means of sonic welding.

15. A method according to claim 13 wherein said hypodermic needle is covered by a moulded cover assembly.

16. A method according to claim 15 wherein said cover assembly is secured to said syringe by means of sonic welding.

17. A method according to claim 13 wherein filling said needle with medicament further comprises:
(a) inserting a pin into said ampul;
(b) injecting medicament into said ampul through said pin;
(c) withdrawing said pin from said ampul; and
(d) establishing an integral wall continuum of said ampul after withdrawal of said pin by means of sonic welding.

18. A method for manufacturing and filling a hypodermic syringe, said method comprising:
(a) injection-moulding a preform comprising a neck at one end and a parison at the other end of said preform, said injection-moulding step further including affixing a hypodermic needle in said neck by insert-moulding;
(b) blow-moulding said parison into the form of an ampul;
(c) covering said hypodermic needle;
(d) injecting medicament into said ampul through the wall thereof; and
(e) establishing an integral continuum of said wall at the point of injection.

19. A method for manufacturing and filling an ampul adapted for use with a hypodermic needle to form a hypodermic syringe, said method comprising:
(a) injection-moulding a preform comprising a neck at one end and a parison having an open end at the other end thereof;
(b) blow-moulding the parison into the form of an ampul;
(c) introducing a medicament into said ampul through a wall thereof, and
(d) establishing an integral continuum of said ampul wall at the point of introduction.

20. A method according to claim 19 wherein step (b) further comprises:
closing said open end around a pin;
injecting blow gas into said ampul through said pin; and
withdrawing said pin from said ampul.

21. A method according to claim 19 wherein step (c) further comprises:
inserting a pin into said ampul;
injecting medicament into said ampul through said pin;
withdrawing said pin from said ampul; and
establishing said integral wall continuum of said ampul after withdrawal of said pin by means of sonic welding.

* * * * *

UNITED STATES PATENT AND TRADEMARK OFFICE
CERTIFICATE OF CORRECTION

PATENT NO. : 4,342,184
DATED : August 3, 1982
INVENTOR(S) : William F. Van Eck; Mauritis J.H. Van Eck It is certified that error appears in the above-identified patent and that said Letters Patent are hereby corrected as shown below:

Column 8, Claim 13, Line 62:   Insert -- (e) -- before the first word of clause "introducing"

Signed and Sealed this

Eighth Day of March 1983

[SEAL]

Attest:

GERALD J. MOSSINGHOFF

Attesting Officer    Commissioner of Patents and Trademarks